United States Patent
Kopelman et al.

(10) Patent No.: US 10,543,066 B2
(45) Date of Patent: Jan. 28, 2020

(54) METHOD AND SYSTEM FOR FABRICATING A DENTAL COPING, AND A COPING FABRICATED THEREBY

(71) Applicant: Align Technology, Inc., San Jose, CA (US)

(72) Inventors: Avi Kopelman, Palo Alto, CA (US); Eldad Taub, Reut (IL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 108 days.

(21) Appl. No.: 15/811,331

(22) Filed: Nov. 13, 2017

(65) Prior Publication Data

US 2018/0132981 A1   May 17, 2018

Related U.S. Application Data

(63) Continuation of application No. 14/720,426, filed on May 22, 2015, now Pat. No. 9,844,429, which is a continuation of application No. 13/620,057, filed on Sep. 14, 2012, now Pat. No. 9,069,914, which is a continuation of application No. 13/189,398, filed on Jul. 22, 2011, now Pat. No. 8,301,287, which is a continuation of application No. 12/149,102, filed on Apr. 25, 2008, now Pat. No. 7,996,099, which is a continuation of application No. 11/498,791, filed on Aug. 4, 2006, now Pat. No. 7,383,094, which is a continuation of application No. 11/214,882, filed on
(Continued)

(51) Int. Cl.
*A61C 13/00* (2006.01)
*G06F 17/50* (2006.01)
*B33Y 50/02* (2015.01)
*G05B 19/4097* (2006.01)
*A61C 13/20* (2006.01)

(52) U.S. Cl.
CPC ......... *A61C 13/0004* (2013.01); *B33Y 50/02* (2014.12); *G05B 19/4097* (2013.01); *G06F 17/50* (2013.01); *A61C 13/20* (2013.01); *G05B 2219/45167* (2013.01)

(58) Field of Classification Search
None
See application file for complete search history.

(56) References Cited

U.S. PATENT DOCUMENTS 2,467,432 A   4/1949   Kesling
3,407,500 A   10/1968  Kesling
(Continued)

FOREIGN PATENT DOCUMENTS

AU   3031677 A   5/1979
AU   517102 B2   7/1981
(Continued)

OTHER PUBLICATIONS

AADR. American Association for Dental Research, Summary of Activities, Mar. 20-23,1980, Los Angeles, CA, p. 195.
(Continued)

*Primary Examiner* — Ryan A Jarrett
(74) *Attorney, Agent, or Firm* — Wilson Sonsini Goodrich & Rosati

(57) ABSTRACT

A wax model of a required coping is produced using CNC machining techniques based on a virtual model of the coping created from digital data obtained from the intraoral cavity. The dental coping is then fabricated from the wax model.

21 Claims, 4 Drawing Sheets

Related U.S. Application Data

Aug. 31, 2005, now Pat. No. 7,110,844, which is a continuation of application No. 10/814,653, filed on Apr. 1, 2004, now Pat. No. 6,957,118.

(60) Provisional application No. 60/459,624, filed on Apr. 3, 2003.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,411,626 A | 10/1983 | Becker et al. |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,092,022 A | 3/1992 | Duret |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,266,030 A | 11/1993 | Van Der Zel |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,378,154 A | 1/1995 | Van Der Zel |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,652,709 A | 7/1997 | Andersson et al. |
| 5,655,653 A | 8/1997 | Chester |
| 5,683,243 A | 11/1997 | Andreiko et al. |
| 5,691,905 A | 11/1997 | Dehoff et al. |
| 5,692,894 A | 12/1997 | Schwartz et al. |
| 5,718,585 A | 2/1998 | Dehoff et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,066,274 A | 5/2000 | Antonson et al. |
| 6,068,482 A | 5/2000 | Snow |
| 6,099,314 A | 8/2000 | Kopelman et al. |
| 6,123,544 A | 9/2000 | Cleary |
| 6,126,732 A | 10/2000 | Hofmann et al. |
| 6,152,731 A | 11/2000 | Jordan et al. |
| 6,174,168 B1 | 1/2001 | Dehoff et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |

(56) References Cited

U.S. PATENT DOCUMENTS

| | | | |
|---|---|---|---|
| 6,244,861 | B1 | 6/2001 | Andreiko et al. |
| 6,309,215 | B1 | 10/2001 | Phan et al. |
| 6,315,553 | B1 | 11/2001 | Sachdeva et al. |
| 6,322,359 | B1 | 11/2001 | Jordan et al. |
| 6,334,853 | B1 | 1/2002 | Kopelman et al. |
| 6,350,120 | B1 | 2/2002 | Sachdeva et al. |
| 6,364,660 | B1 | 4/2002 | Durbin et al. |
| 6,382,975 | B1 | 5/2002 | Poirier |
| 6,398,548 | B1 | 6/2002 | Muhammad et al. |
| 6,398,554 | B1 | 6/2002 | Perot et al. |
| 6,402,707 | B1 | 6/2002 | Ernst |
| 6,482,298 | B1 | 11/2002 | Bhatnagar |
| 6,488,503 | B1 | 12/2002 | Lichkus et al. |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,594,539 | B1 | 7/2003 | Geng |
| 6,629,840 | B2 | 10/2003 | Chishti et al. |
| 6,640,150 | B1 | 10/2003 | Persson et al. |
| 6,705,863 | B2 | 3/2004 | Phan et al. |
| 6,722,880 | B2 | 4/2004 | Chishti et al. |
| 6,957,118 | B2 | 10/2005 | Kopelman et al. |
| 7,110,844 | B2 | 9/2006 | Kopelman et al. |
| 7,112,065 | B2 | 9/2006 | Kopelman et al. |
| 7,234,938 | B2 | 6/2007 | Bodenmiller |
| 7,383,094 | B2 | 6/2008 | Kopelman et al. |
| 7,996,099 | B2 | 8/2011 | Kopelman et al. |
| 8,301,287 | B2 | 10/2012 | Kopelman et al. |
| 9,069,914 | B2 | 6/2015 | Kopelman et al. |
| 9,844,429 | B2 | 12/2017 | Kopelman et al. |
| 2001/0034010 | A1 | 10/2001 | MacDougald et al. |
| 2002/0006597 | A1 | 1/2002 | Andreiko et al. |
| 2002/0015934 | A1 | 2/2002 | Rubbert et al. |
| 2002/0028418 | A1 | 3/2002 | Farag et al. |
| 2002/0058229 | A1 | 5/2002 | Sugimoto |
| 2002/0102519 | A1 | 8/2002 | Baum et al. |
| 2002/0102521 | A1 | 8/2002 | Iiyama et al. |
| 2002/0137011 | A1 | 9/2002 | Shoher et al. |
| 2003/0009252 | A1 | 1/2003 | Pavlovskaia et al. |
| 2003/0096210 | A1 | 5/2003 | Rubbert et al. |
| 2003/0096214 | A1 | 5/2003 | Luthardt et al. |
| 2003/0116299 | A1 | 6/2003 | Embert et al. |
| 2003/0123943 | A1 | 7/2003 | Hamada |
| 2003/0139834 | A1 | 7/2003 | Nikolskiy et al. |
| 2003/0152884 | A1 | 8/2003 | Wiechmann et al. |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2013/0103176 | A1 | 4/2013 | Kopelman et al. |

FOREIGN PATENT DOCUMENTS

| | | |
|---|---|---|
| AU | 5598894 A | 6/1994 |
| CA | 1121955 A | 4/1982 |
| CA | 2356631 A1 | 2/2003 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-9962422 A1 | 12/1999 |
| WO | WO-0008415 A1 | 2/2000 |
| WO | WO-0141670 A1 | 6/2001 |
| WO | WO-02071306 A1 | 9/2002 |
| WO | WO-02076326 A2 | 10/2002 |
| WO | WO-03017864 A1 | 3/2003 |
| WO | WO-2004008981 A2 | 1/2004 |
| WO | WO-2004030565 A1 | 4/2004 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Operation & Training Manual. Great Lakes Orthodontics, Ltd. 199 Fire Tower Drive, Tonawanda, New York. 14150-5890, 20 pages total (1990).

(56) References Cited

OTHER PUBLICATIONS

Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the lnvisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).

DENT-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
European office action dated Feb. 2, 2016 for EP Application No. 04724343.1.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URLhttp://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).

(56) References Cited

OTHER PUBLICATIONS

JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Kuwata, et al.. Color Atlas of Ceramo-Metal Technology. Ishiyaku EuroAmerica, Inc. 1986, pp. 96-101.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Office action dated Jan. 31, 2012 for U.S. Appl. No. 13/189,398.
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).

(56) References Cited

OTHER PUBLICATIONS

Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,<http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile!Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
TRU-TAIN Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).

METHOD AND SYSTEM FOR FABRICATING A DENTAL COPING, AND A COPING FABRICATED THEREBY

CROSS-REFERENCES TO RELATED APPLICATIONS

This application is a continuation of U.S. application Ser. No. 14/720,426, filed May 22, 2015, now U.S. Pat No. 9,844,429, which is a continuation of U.S. application Ser. No. 13/620,057, filed on Sep. 14, 2012, now U.S. Pat. No. 9,069,914, which is a continuation of U.S. application Ser. No. 13/189,398, filed on Jul. 22, 2011, now U.S. Pat. No. 8,301,287, which is a continuation of U.S. application Ser. No. 12/149,102, filed on Apr. 25, 2008, now U.S. Pat. No. 7,996,099, which is a continuation of U.S. application Ser. No. 11/498,791, filed on Aug. 4, 2006, now U.S. Pat. No. 7,383,094, which is a continuation of U.S. application Ser. No. 11/214,882, filed on Aug. 31, 2005, now U.S. Pat. No. 7,110,844, which is a continuation of U.S. application Ser. No. 10/814,653, filed on Apr. 1, 2004, now U.S. Pat. No. 6,957,118, claiming the benefit under 35 USC § 119(e) of U.S. Provisional Application No. 60/459,624, filed on Apr. 3, 2003, the entire contents of each of which is hereby incorporated herein by reference in their entirety.

FIELD OF THE INVENTION

This invention relates to teeth restoration, specifically to a method and system for fabricating dental copings for crowns and/or bridges, and to the copings made thereby.

BACKGROUND OF THE INVENTION

In the field of teeth restoration, metal copings are typically used in the construction of a dental crown and/or bridge. The metal coping functions as the understructure of the crown, and is typically covered with a coating of ceramic porcelain composition or a polymer-based veneering material. The metal coping supports the coating and provides the required structural strength and rigidity for the restored tooth to resist the forces of mastication.

There are methods in the art for the production of metal coping by casting it from a wax pattern, for example by the known "lost wax" technique. An accurate working model of the patient's teeth, which includes the preparation (die) of the tooth (or teeth) to be restored and its surrounding area, is used. As discussed in Kuwata et al., Color Atlas of Ceramo-Metal Technology (Ishiyaku EuroAmerica, Inc., 1986, pp. 96-101), a wax coping, which is an exact replication of the desired metal coping, is manually built by wrapping a thin sheet of wax around the working model of the preparation, and is adapted to the preparation surface. By using a heated carving knife, the margin of the adapted sheet wax is cut off and the sheet joints are bent and sealed by adding more wax. The wax margin is further processed in order to correspond to the margin line of the restoration, i.e. by additional carving and/or wax adding.

The finished wax-up of the coping is then removed from the working model and invested in a material that solidifies onto the external side of the wax coping and forms a mold (this stage is known as the "investment" stage). The combined structure is then heated such that the wax is burnt out, leaving a cavity into which the metal is cast. After hardening, the mold is removed from the metal casting.

Another method for producing metal coping involves a direct fabrication of the metal coping based on digital data. U.S. 2002/0137011 discloses an automated and digital method for the formation of the metal coping from a sheet of metallic material, which comprises: scanning a three dimensional image of the die of the tooth or teeth to be restored; digitizing the scanned three dimensional image into digital information, storing the digital information in a computer; feeding the digital information from the computer into a CNC (computerized numerical control) cutting machine; cutting out a section of material of metallic composition into a two dimensional configuration representing a two dimensional lay out of the scanned three dimensional image, adapting the cut out section of material over the die so that the material covers the die surface in close engagement therewith to form a single three dimensional structure having the shape of the die and heat treating the structure, into a coping, conforming in shape to the die.

WO 03/017864 discloses a method for producing a dental prosthesis such as a dental coping. The method comprises the following steps: obtaining three-dimensional digital data relating to a patient's dentition; designing a virtual prosthesis for the dentition using the three-dimensional digital data; transmitting digital data corresponding to the virtual prosthesis to an automated prototyping system; producing a prototype of the dental prosthesis with the automated prototyping system, the prototype made of a material that can be ablated; covering at least the prototype with a hardening material and removing the prototype from within said hardening material to produce a mold for the dental prosthesis; casting the dental prosthesis by filling the mold with a metal and removing the hardening material.

In the case of coping fabrication in the "lost wax" technique, be it the manual production or the automated, prototype production, the wax is used as it is easy to manipulate and allows a high level of accuracy. Typically, soft wax, i.e. wax with relatively high viscosity, is used. Special care must be taken in handling the soft wax, as it is very sensitive to physical stress. Indeed, any damage to the wax-up pattern before investment (i.e. during its production process or after) may lower the quality of the replicated dental coping.

Of general background interest, the following patents describe manufacturing methods for prostheses. In U.S. Pat. Nos. 4,663,720 and 4,742,464 an apparatus and method are disclosed for designing a prosthesis starting with a 3D model of the patient's dentition obtained by optical methods, and directly machining the prosthesis from a blank. In U.S. Pat. No. 5,092,022, a prosthesis or a negative mold therefor can be machined automatically from suitable materials, with the assistance of a computer which takes into consideration, inter alia, the shape of the zone of implantation previously obtained. In U.S. Pat. No. 5,452,219, a negative mold for a prosthesis is milled using a machine controlled by a program based on 3D data obtained from a tooth model. In U.S. Pat. No. 5,378,154 a method for machining a dental prosthesis is disclosed, wherein the outside visible part of the prosthesis is subjected to a material removal operation by means of a CNC machining tool which follow machining paths that follow 3D irregularly spaced curved lines. In U.S. Pat. No. 6,126,732, a shaped high-strength dental ceramic prosthesis is made by pressing a molding composition comprising 1-50 wt % glass particles and about 50-99 wt % ceramic particles to form a ceramic frame, veneering the frame and firing the coated frame. In U.S. Pat. Nos. 5,691,905 and 5,718,585 methods of milling and polishing a set of negative mold parts are disclosed. In U.S. Pat. No. 6,488,503, a process is described for producing an artificial tooth, in which polymerizable materials are injection molded into a mold in stages to produce a solid core applied on an inner layer, which is applied on an external layer of the artificial tooth. In U.S. Pat. No. 6,066,274, a device including an injection molding tool is disclosed for producing a sinterable ceramic and/or metallic product using engageable molding tool parts one of which is produced using a wet composition. In U.S. Pat. No. 5,382,164, a method of making restorations is disclosed, comprising: temporarily repairing a tooth area to be restored to a final shape, and taking a first impression of the tooth area to be restored; preparing the tooth to be restored, and taking a second impression within the first impression to form a physical model of the crown. This model is then scanned to provide an image thereof, and a computer uses this image to mill the final restoration.

SUMMARY OF THE INVENTION

The present invention provides, in its first aspect, a method and system for fabricating a dental coping for dental prosthesis of at least one tooth which is to be fitted over a tooth preparation. The method comprises providing three-dimensional (3D) digital data relating to the patient's dentition, which includes data representative of the surface topology of the preparation and its surroundings. The method further comprises generating a three-dimensional (3D) virtual model of a dental coping for the tooth, such that the inner surface of the virtual coping fits over a portion of the surface of the tooth preparation in close engagement. Alternatively, a virtual model of the final required restoration may be created, and the internal surface of the required coping is derived from this model; a suitable external surface for the coping can be designed in any suitable manner. The method further comprises generating a computerized numerical control (CNC) set of instructions corresponding to the 3D model of said coping. Based on said set of instructions, a model coping is fabricated from wax or other low fusion temperature material, by a computerized numerical control (CNC) milling machine. From the fabricated coping wax model, a dental coping is fabricated. The system comprises means for providing three-dimensional (3D) digital data relating to the patient's dentition, which includes data representative of the surface topology of the preparation and its surroundings. The system further comprises means for generating a three-dimensional (3D) virtual model of a dental coping for the tooth, such that the inner surface of the virtual coping fits over a portion of the surface of the tooth preparation in close engagement. The system further comprises means for generating a computerized numerical control (CNC) set of instructions corresponding to the 3D model of said coping. The system also comprises mans for fabricating a model of the coping from wax or other low fusion temperature material, by a computerized numerical control (CNC) milling machine, based on said set of instructions. The system further comprises means for fabricating a dental coping from the fabricated coping wax model.

The present invention also provides a method and system for the fabrication of a coping wax model that is to be used for fabricating a dental coping for a dental prosthesis of at least one tooth that is to be fitted over a tooth preparation. This method comprises providing three-dimensional (3D) digital data relating to the patient's dentition, which includes data representative of the surface topology of the tooth preparation and its surroundings; generating a three-dimensional (3D) virtual model of a dental coping for the tooth, such that the inner surface of the virtual coping fits over a portion of the surface of the tooth preparation in close engagement; generating a computerized numerical control (CNC) set of instructions corresponding to the 3D model of said coping; and based on said set of instructions, fabricating a wax coping by a computerized numerical control (CNC) milling machine. The system comprises means for providing three-dimensional (3D) digital data relating to the patient's dentition, which includes data representative of the surface topology of the tooth preparation and its surroundings; means for generating a three-dimensional (3D) virtual model of a dental coping for the tooth, such that the inner surface of the virtual coping fits over a portion of the surface of the tooth preparation in close engagement; means for generating a computerized numerical control (CNC) set of instructions corresponding to the 3D model of said coping; and based on said set of instructions, means for fabricating a wax coping by a computerized numerical control (CNC) milling machine.

The term "tooth preparation" as used herein refers both to one or more tooth stumps or pivots (also known as cores or posts) prepared by the care provider on the basis of an original tooth or an implant which serves as a basis for the dental prosthesis (e.g. crown or bridge).

The term "dental coping" as used herein refers to a support structure for a crown, i.e. structure that cups only one tooth, as well as a support structure for a bridge, i.e. structure that cups more than one tooth. The term "dental coping" as used herein, also refers to the cup, which may be made from metals or ceramics, for example, and all other prosthesis elements such as connectors and pontics, as the case may be. The dental coping may be fabricated from suitable materials such as metal, ceramo-metal materials, etc.

The 3D digital data may be obtained by a number of ways known per se. For example, such digital data may be obtained in a manner as described in WO 00/08415, U.S. Patent Application No. 2002/0137011 or in any of U.S. Pat. Nos. 6,099,314 and 6,334,853, or any combination thereof. The 3D data includes the surface topology of the preparation, as well as its surroundings. Furthermore, such 3D digital data may also comprise other data, for example, data that was added by the orthodontist or a dental technician, such as the preparation's finish line.

The 3D virtual model of the dental coping may be produced in a number of ways. By one example, the dentist, orthodontist, etc. (to be referred to herein collectively as the "care provider") designs the overall outer surface of the tooth prosthesis and then, based on known considerations of enamel thickness as well as coping thickness, the coping is designed so as to fit below the surface of the tooth prosthesis and over the tooth preparation. As known per se, some room needs to be reserved for adhesive materials.

By another example, the coping is designed primarily on the basis of the surface topology of the preparation and other factors such as the coping wall's thickness, finish line data, etc.

The generation of the virtual 3D coping data may be automatic, manual or a combination thereof.

The term "wax" includes any material that is relatively hard and lends itself to machining, particularly milling, while having a sufficient low melting point and appropriate kinematic viscosity that renders it suitable for use in a lost wax process or the like.

The wax that should be used in accordance with the invention is hard and durable that lends itself to milling in a milling machine. Another requirement of the wax is that after melting, it should have a viscosity sufficiently low to be usable in a lost wax technique known per se in the art of metal casting.

A typical wax that can be used in accordance with the invention is such having a melting point and congealing point of 55-80° C. and a kinematic viscosity of less than 90 m² sec. at about 100° C.

As will be appreciated, the coping prepared in accordance with the invention may be suitable for a single tooth, (in the case of a single tooth prosthesis), or a coping that serves as a basis for a bridge.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1A:
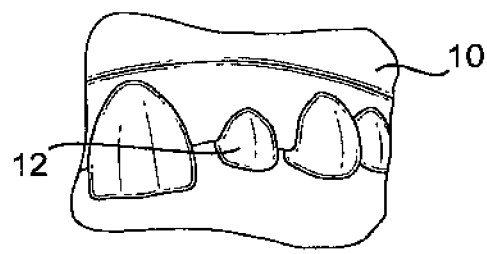
FIGS. 1A-1E illustrate an exemplary scenario for the fabrication of a dental coping in which the invention is implemented.

FIGS. 1A-1E illustrate an exemplary scenario for the fabrication of a dental coping in which the invention is implemented. The scenario is carried out with the aid of a computer system, the operation of which will be explained later on. FIG. 1A shows a section 10 of a patient's teeth (part of the patient's upper jaw, in this example), in which tooth prosthesis is to be fitted over tooth preparation 12. In the example of FIG. 1A, the root and base of the tooth 12 are sufficiently strong and healthy, and the care provider prepared the tooth for the crown by removing a portion of the enamel and dentin. If the tooth to be restored is severely decayed or weak, then it may be necessary to insert a metal implant or pivot (also known as cores or posts) by any one of a number of ways known per se.

Figure 3:
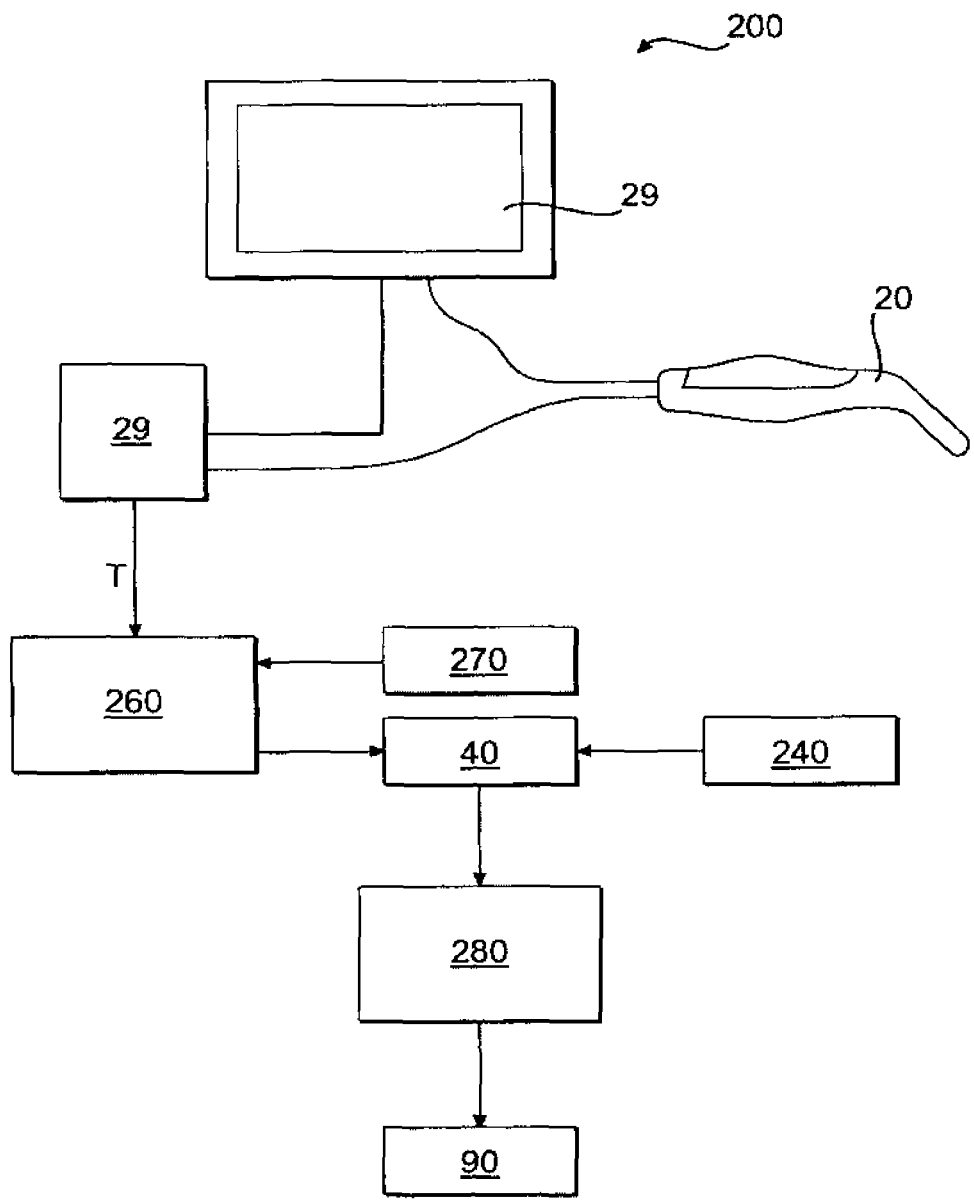
FIG. 3 shows a block diagram of fabrication system according to the invention.

An exemplary system 300 for carrying out the process of the invention is illustrated in FIG. 3.

The 3D digitized data of the intraoral cavity, including the dentition and associated anatomical structures of a patient is obtained, and thus suitable equipment for scanning a patient's teeth is used by the care provider to acquire the 3D data. The production of the virtual 3D working model of the preparation and its surroundings is known per-se.

Figure 1B:
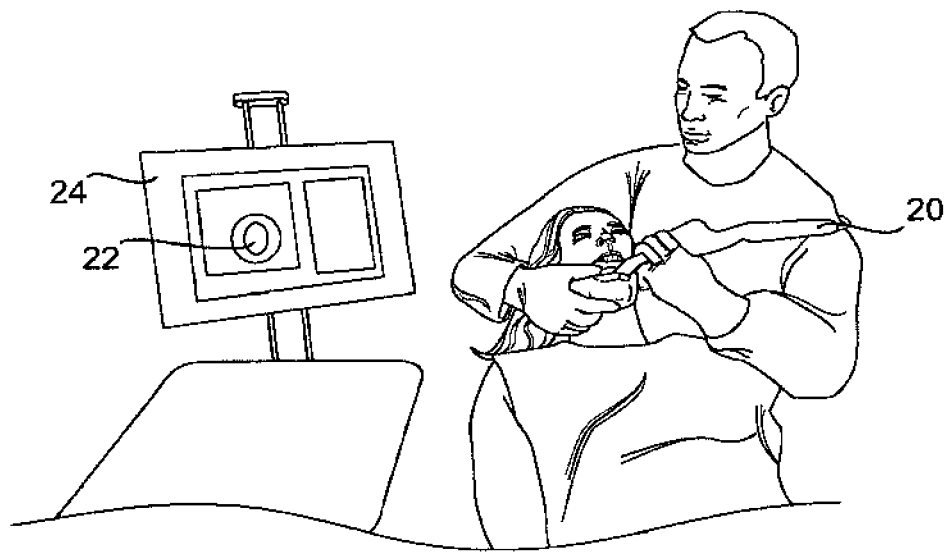

As shown in FIG. 1B, for example, the care provider captures an image of the preparation and its surroundings with a probing device 20. Advantageously, a probe for determining three dimensional structure by confocal focusing of an array of light beams may be used, for example as manufactured under the name of PROSTHOCAD or as disclosed in WO 00/08415, the contents of which are incorporated herein in their entirety. Alternatively, scanning of the dental cavity to provide the 3D data may be accomplished using a suitable apparatus, for example as disclosed in any one of U.S. Pat. Nos. 4,837,732, 4,611,288, 6,594,539, 6,402,707, 6,364,660,US 2002/0028418, US 2002/0058229, U.S. Pat. Nos. 5,652,709, 4,575,805, 5,733,126, 5,880,962, 4,742,464, 4,663,720, WO 02/071306 mutatis mutandis. The contents of these publications are incorporated herein in their entirety by reference thereto.

The 3D data obtained by the probe may then be stored in a suitable storage medium, for example a memory in a computer workstation, for further processing, as described herein.

Alternatively, a negative cast or impression is taken of the patient's teeth, in a manner known in the art, and this negative model and a positive cast is made from this model suitable for scanning. The positive cast may be scanned by any method known in the art, including using the aforesaid probe manufactured under the name of PROSTHOCAD or as disclosed in WO 00/08415. Alternatively, the negative model itself may be scanned.

Alternatively, a composite positive-negative model may be manufactured from the original negative model. Thereafter, the positive-negative model may be processed to obtain 3D digitized data, for example as disclosed in U.S. Pat. No. 6,099,314, assigned to the present assignee, and the contents of which are incorporated herein in their entirety.

Alternatively, the 3D digitized data may be obtained in any other suitable manner, including other suitable intra oral scanning techniques, based on optical methods, direct contact methods or any other means, applied directly to the patient's dentition. Alternatively, X-ray based, CT based, MRI based, or any other type of scanning of the patient or of a positive and/or negative model of the intra-oral cavity may be used. The digitized data may be associated with a complete dentition, or of a partial dentition, for example such as a preparation only of the intra oral cavity.

Referring to FIG. 3, a virtual 3D working model 22 is digitally produced by a processor, 29 and may well be displayed on display 24.

Figure 1C:
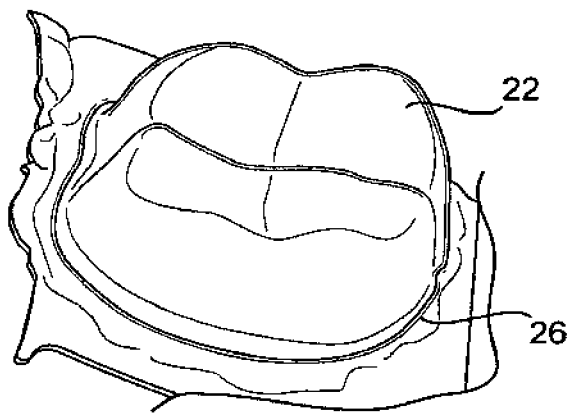
Figure 1D:
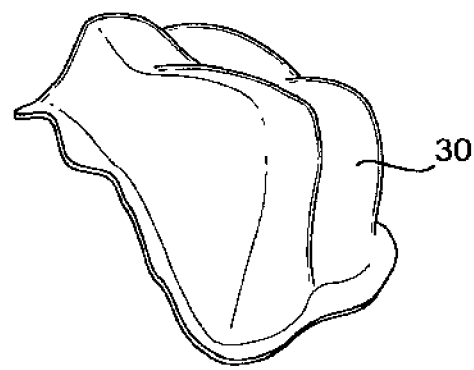
Figure 1E:
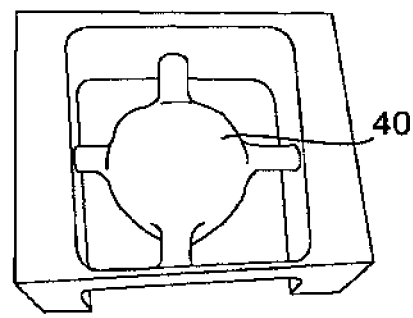

FIG. 1C shows the virtual working model 22 in a magnified manner, with its finish line 26 (also known as the margin line) that was either generated automatically or marked by the care provider. The virtual model 22 and the finish line 26 data, and perhaps additional 3D data that relates to the patient's dentition, are processed and then input to a CAD (Computer-Aided Design) unit (not shown) that allows for the digital design of the dental coping, resulting in the virtual coping 30, shown in FIG. 1D.

The virtual coping 30 may then be further processed by a CAM (Computer-Aided Manufacture) unit (not shown) to generate a digital set of instructions T that are fed into a CNC (computerized numerical control) milling machine 260, from which a wax coping 40 (as the one shown in FIG. 1E) is milled using wax or the like supplied from supply 270. Wax coping 40 is made of relatively hard, durable wax or similar material. In particular, the coping 40 is made from a material that on the one hand lends itself to milling in a milling machine, while on the other hand has a low melting point and after melting, it has a kinematic viscosity sufficiently low to be usable in a lost wax technique known per se in the art of metal casting. Preferably, such a material has a melting point and congealing point of about 55° C. to about 80° C. and a kinematic viscosity of less than 90 m² sec. at about 100° C.

The desired dental coping 90 is then produced from the wax coping, according to common dental practice, via suitable manufacturing means 280.

The finish line data can be generated for example, in a manner disclosed in U.S. Ser. No. 10/623,707 and WO 04/008981 also assigned to the present assignee, and the contents of which are incorporated herein in their entirety. Alternatively, the finish line may be generated using methods disclosed in U.S. Pat. No. 5,266,030 the contents of which are incorporated herein. The virtual generation of the finish line may be incorporated as an integral component in the method of the invention.

The additional 3D data that relates to the patient's dentition includes, inter-alia, information relating to the surrounding of the tooth to be restored, e.g. 3D representation of the patient's dentition, including the upper and lower jaws and their occlusion relationship. Such information is needed, e.g. for the design of the dental crown, and can be generated for example, as disclosed in U.S. Pat. Nos. 6,099,314 and 6,334,853.

The virtual model of the desired coping can be generated in several ways. According to one possible way, the care provider designs the overall outer surface of the tooth prosthesis, based on known considerations such as enamel thickness, as well as coping thickness and others. The coping is designed so as to fit below the surface of the tooth prosthesis and over the tooth preparation. By another example, the coping is designed primarily on the basis of the surface topology of the preparation and other factors such as the coping wall's thickness, finish line data, etc.

In particular, the external surface of the coping, which eventually mates with a cap or the like which may be single-layered or multi-layered, is designed according to predetermined criteria, as known in the art, to provide the required mechanical properties required from the restoration.

The virtual coping 30 may also be created in other ways. For example, a physical model of the restoration may be created in any suitable manner, for example as disclosed in U.S. Pat. No. 5,382,164, the contents of which are incorporated herein in their entirety. The inner surface of such a model, preferably including the finish line, may be scanned in any suitable manner, similar, for, example to that described above for the preparation, mutatis mutandis, Alternatively, a virtual model of the full restoration may be used to provide the internal surface and preferably the finish line for the coping. Then, an external surface for the coping may be designed according to any suitable criteria, for example as described above, and the virtual model corresponding to the external surface may be joined to the virtual model of the inner surface to provide the virtual coping 30.

The method of the present invention in fact makes use of the "lost wax" technique, by utilizing relatively hard, durable wax, which can be milled to the desired pattern by a CNC milling machine.

Figure 2:
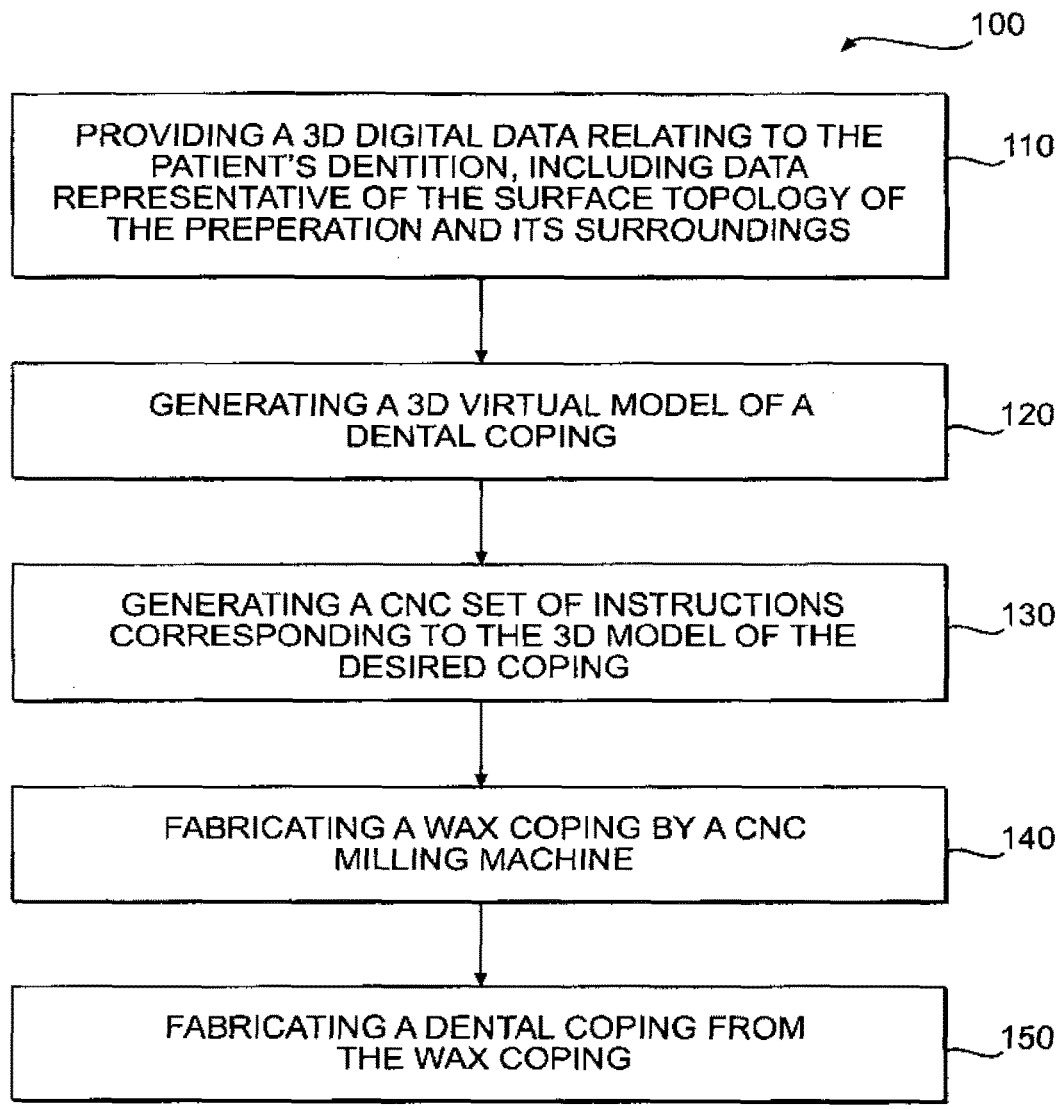
FIG. 2 shows a block diagram of fabrication processes according to the invention.

FIG. 2 shows a block diagram of fabrication processes 100 according to the invention. At step 110, a three-dimensional (3D) digital data is provided. The 3D digital data relates to the patient's dentition, including data representative of the surface topology of the preparation and its surroundings. At step 120, a 3D virtual model of a dental coping is generated.

At step 130, a CNC (Computerized Numerical Control) set of instructions corresponding to the 3D virtual model of the desired coping is generated, and fed into a CNC milling machine for the fabrication of a wax coping (step 140), wherein a wax coping is produced from a suitable block of wax or the like.

Optionally, and particularly when the final prosthesis is a bridge, wax replicas of suitable connectors and/or one or more pontics are made, either manually or by any suitable method, including machining, casting and so on, indicated at 240 in FIG. 3. Then, the connectors and/or pontics are joined to the wax copings of the abutment teeth in a suitable manner, for example as is known in the art per se. The metal or ceramic structure for the bridge is then made from the wax model thereof in a similar manner to that described below for a single coping, mutatis mutandis.

At step 150, the dental coping is fabricated from the wax coping. This may be accomplished in any number of ways, known per se in the art. For example, the wax coping is invested in a material that solidifies onto the external side of the wax coping and forms a mold. After the investment stage, the combined structure is then heated such that the wax is burnt out, leaving a cavity. Into this cavity, a suitable molten metal may be injected, and after hardening, the mold is removed from the metal casting to provide a metal coping. Such a lost wax process may be similar to the process used for the production of restorations as described by Ivoclar Vivadent Ltd. regarding the IPS Empress system in http://www.ivoclar.co.uk/technician/nonmetal2.html, mutatis mutandis, for example Alternatively, a suitable ceramic molding composition may be pressed into the cavity, for example as described in U.S. Pat. No. 6,126,732, mutatis mutandis, the contents of which are incorporated herein in their entirety. Alternatively, sintering methods may be applied to the mold to produce a ceramic coping.

Alternatively, the wax coping may be scanned and the coping produced in a manner similar to the production of crowns and bridges, as described by DeguDent regarding the Cercon system in http://www.degudent.com/Products/Cercon_smart_ceramics/index.asp, mutatis mutandis.

The dental coping manufactured according to the present invention is thus derived from a wax model, which due to its relatively softness can be machined to a smoother surface texture than is possible when machining the coping directly from the desired final material such as metal or a ceramic. Accordingly, dental copings produced using the method of the invention using the wax for preparing a mold are correspondingly smoother, and furthermore it is possible to include fine details in the final coping, with respect to copings produced using direct material removal methods applied to the final material.

Furthermore, the wax-based method of the present invention for producing the dental coping has some advantages over direct material removal methods that are used elsewhere for producing the coping directly from the desired final material. For example less wear and breakage are experienced by the machining tool, and thus lowers costs. Furthermore, deformations of the tool, when a direct contact tool such as for example a mechanical tool is used, is less likely, and thus less deviations from the nominal dimensions of the coping with respect to the virtual model thereof occur than when producing a coping directly from a metal or other hard material.

The invention allows to gather the 3D data that represents the patient's dentition in one place (say, the care provider's clinic), to design the virtual coping model at the clinic or at a remote location, to generate the CNC set of instructions at another place and to fabricate the wax coping at a yet another location. Furthermore, the invention allows for the fabrication of the wax coping and the dental coping at different locations without damaging the quality of the dental coping due to deformations in the coping wax model. It should be noted that additional, intermediate steps in which digital data is transmitted between remote locations might be carried-out as part of method 100, for example between steps 110 and 120, etc.

The invention is not bound by the specified example of FIGS. 1A-1E and, accordingly, other scenarios may be used in addition or in lieu of the above, depending upon the particular application. Specifically, the invention can also be utilized in a less "digitized" scenario, for example one in which the care provider gathers the relevant information relating to the patient's dentition in a non-digitized manner (e.g. by taking a physical impression of the patient's dentition), and the patient's dentition data is digitized later on, at a laboratory.

Furthermore, the invention can be utilized for the fabrication of the dental prostheses as a whole, as needed, for example, when restoring the tooth with a gold prosthesis. In that case, a wax model of the desired prosthesis is fabricated, from which a whole metal prosthesis is replicated.

What is claimed is:

1. A system for fabricating a model of a dental coping shaped to fit over a tooth preparation in a patient's intraoral cavity, the system comprising:
    a milling machine configured to fabricate a model of the dental coping; and
    one or more computer-readable storage media comprising instructions that, when executed by a processor, cause the processor to:
    receive 3D digital data of the patient's intraoral cavity, the 3D digital data comprising an enamel thickness of a tooth preparation,
    generate a 3D virtual model of an inner surface of a restoration;
    generate a 3D virtual model of a dental coping having an external surface based on the 3D digital data comprising the enamel thickness of the tooth preparation and an inner surface based on the 3D virtual model of the inner surface of the restoration,
    generate instructions for fabricating the model of the dental coping based on the 3D virtual model of the dental coping, and
    transmit the instructions to the milling machine.

2. The system of claim 1, wherein generating the 3D virtual model of the inner surface of a restoration comprises scanning an inner surface a physical restoration.

3. The system of claim 2, wherein generating the 3D virtual model of the inner surface of a restoration comprises scanning a finish line of the physical restoration.

4. The system of claim 1, wherein generating the 3D virtual model of the dental coping further comprises joining the 3D virtual model of the inner surface of the restoration with the 3D digital data comprising the enamel thickness of the tooth preparation.

5. The system of claim 1, wherein the model of the dental coping is configured to be used in a lost wax process for fabricating the dental coping.

6. The system of claim 5, wherein the dental coping comprises material with one or more of: a melting point from about 55° C. to about 80° C., a congealing point from about 55° C. to about 80° C., or a kinematic viscosity of less than about 90 m²/sec at about 100° C.

7. The system of claim 1, wherein the 3D virtual model of the dental coping comprises finish line data corresponding to a finish line of the tooth preparation.

8. The system of claim 1, wherein the 3D virtual model of the dental coping is generated according to a coping thickness for the dental coping.

9. The system of claim 1, wherein the 3D digital data comprises surface topology data of the patient's intraoral cavity.

10. The system of claim 1, wherein the tooth preparation comprises one or more tooth stumps, implants, or pivots.

11. The system of claim 1, wherein the restoration comprises a crown prosthesis or a bridge prosthesis.

12. A method for fabricating a model of a dental coping shaped to fit over a tooth preparation in a patient's intraoral cavity, the method comprising:
    receiving 3D digital data of the patient's intraoral cavity, the 3D digital data comprising an enamel thickness of a tooth preparation;
    generating a 3D virtual model of an inner surface of a restoration;
    generating a 3D virtual model of a dental coping having an external surface based on the 3D digital data comprising an enamel thickness of a tooth preparation and an inner surface based on the 3D virtual model of the inner surface of the restoration;
    generating instructions for fabricating the model of the dental coping based on the 3D virtual model of the dental coping; and
    transmitting the instructions to a milling machine, the instructions configured to cause the milling machine to fabricate the model of the dental coping.

13. The method of claim 12, wherein generating the 3D virtual model of the inner surface of the restoration comprises scanning an inner surface of a physical restoration.

14. The method of claim 12, wherein generating the 3D virtual model of the inner surface of a restoration comprises scanning a finish line of the physical restoration.

15. The method of claim 12, wherein generating the 3D virtual model of the dental coping further comprises joining the 3D virtual model of the inner surface of the restoration with the 3D digital data comprising the enamel thickness of the tooth preparation.

16. The method of claim 12, wherein the wax material comprises one or more of: a melting point from about 55° C. to about 80° C., a congealing point from about 55° C. to about 80° C., or a kinematic viscosity of less than about 90 m²/sec at about 100° C.

17. The method of claim 12, wherein the 3D virtual model of the dental coping comprises finish line data corresponding to a finish line of the tooth preparation.

18. The method of claim 12 wherein the 3D virtual model of the dental coping is generated according to a specified coping thickness for the dental coping.

19. The method of claim 12, wherein the 3D digital data comprises surface topology data of the patient's intraoral cavity.

20. The method of claim 12, wherein the tooth preparation comprises one or more tooth stumps, implants, or pivots.

21. The method of claim 12, wherein the restoration comprises a crown prosthesis or a bridge prosthesis.

* * * * *